United States Patent
Bublitz et al.

(10) Patent No.: US 10,568,503 B2
(45) Date of Patent: Feb. 25, 2020

(54) OPTICAL COHERENCE TOMOGRAPHY FOR PERFORMING MEASUREMENTS ON THE RETINA

(71) Applicant: CARL ZEISS MEDITEC AG, Jena (DE)

(72) Inventors: Daniel Bublitz, Rausdorf (DE); Christoph Nieten, Jena (DE); Lars Omlor, Aalen (DE); Kai Wicker, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 120 days.

(21) Appl. No.: 15/519,378

(22) PCT Filed: Oct. 9, 2015

(86) PCT No.: PCT/EP2015/073326
§ 371 (c)(1),
(2) Date: Apr. 14, 2017

(87) PCT Pub. No.: WO2016/058910
PCT Pub. Date: Apr. 21, 2016

(65) Prior Publication Data
US 2017/0224208 A1    Aug. 10, 2017

(30) Foreign Application Priority Data

Oct. 17, 2014 (DE) .................. 10 2014 115 157

(51) Int. Cl.
*A61B 3/14* (2006.01)
*A61B 3/10* (2006.01)

(52) U.S. Cl.
CPC ................... *A61B 3/102* (2013.01)

(58) Field of Classification Search
CPC ............ G01B 9/02004; G01B 9/02011; G01B 9/02027; G01B 9/02028; G01B 9/02063;
(Continued)

(56) References Cited

U.S. PATENT DOCUMENTS 7,330,270 B2    2/2008 O'Hara et al.
2005/0274894 A1* 12/2005 Fujita .................. A61B 5/0066
250/363.04
(Continued)

FOREIGN PATENT DOCUMENTS

CN    102 819 111 A    12/2012
DE    10 2005 006724 A1    12/2013
WO    WO 2008/139799 A1    11/2008

OTHER PUBLICATIONS

International Preliminary Report on Patentability for corresponding International Application No. PCT/EP2015/073326 dated Apr. 27, 2017; 12 pages.
(Continued)

*Primary Examiner* — Mustak Choudhury
(74) *Attorney, Agent, or Firm* — Patterson Thuente Pedersen, P.A.

(57) ABSTRACT

An optical coherence tomograph includes a wavelength tunable illuminating device, an illumination and measurement beam path with a dividing element and a scanner and a front optical unit and a reference beam path, a detection beam path and a flat panel detector. A beam splitter conducts the separated measurement radiation to the detection beam path and an optical element acts only on the illumination radiation. The optical element sets the numerical aperture of the illumination of the illumination field in the eye. An optical element acts only on the measurement radiation and sets the numerical aperture with which measurement radiation is collected in the eye. An aperture is arranged in front of the flat panel detector in an intermediate image plane and defines the size of an object field. The flat panel detector has a spatial resolution of 4 to 100 pixels in a direction.

22 Claims, 10 Drawing Sheets

(58) Field of Classification Search
CPC ............ G01B 9/02085; G01B 9/02032; G01B 9/02091; G01B 9/02042–02048; G01B 9/02077; G01B 9/02079; G01B 9/02057; G01B 9/0205; G01B 9/02044; G01B 9/02055; G02B 23/2446; G02B 21/0032; G02B 21/0052; G02B 21/361; G02B 21/367; G02B 23/04; G02B 26/06; G02B 26/08; G02B 26/105; G02B 27/0068; G01N 21/47; G01N 21/4795; A61B 3/12; A61B 3/102; A61B 3/117; A61B 3/1005; A61B 3/1015; A61B 1/00096; A61B 1/000167; A61B 1/00172; A61B 1/06; A61B 1/07; A61B 3/14; A61B 5/0066; A61B 5/0068; A61B 5/0075; A61B 5/0084; G01J 9/00
USPC ........ 351/206, 208, 221; 356/457, 479, 497; 359/238; 250/363.04
See application file for complete search history.

(56) References Cited

U.S. PATENT DOCUMENTS

| | | | |
|---|---|---|---|
| 2006/0109477 A1 | 5/2006 | Zhou et al. | |
| 2007/0013918 A1 | 1/2007 | Hauger et al. | |
| 2007/0238955 A1 | 10/2007 | Tearney et al. | |
| 2008/0278687 A1* | 11/2008 | Somani ............... | A61B 3/0075 351/208 |
| 2012/0218557 A1 | 8/2012 | Sugita et al. | |
| 2013/0335706 A1* | 12/2013 | Schmitt-Manderbach ................ | A61B 3/1005 351/221 |
| 2014/0028974 A1* | 1/2014 | Tumlinson ............ | A61B 3/102 351/206 |
| 2015/0037877 A1* | 2/2015 | Peng .................. | G01N 21/6428 435/288.7 |

OTHER PUBLICATIONS

English translation of International Preliminary Report on Patentability for corresponding International Application No. PCT/EP2015/073326 dated Apr. 27, 2017; 16 pages.
International Search Report for corresponding International Application No. PCT/EP2015/073326 dated Dec. 14, 2015; 3 pages.
English translation of International Search Report for corresponding International Application No. International Application No. PCT/EP2015/073326 dated Dec. 14, 2015; 3 pages.
Written Opinion for corresponding International Application No. International Application No. PCT/EP2015/073326 dated Dec. 14, 2015: 9 pages.
Zhihua Ding et al: "High-resolution optical coherence tomography over a large depth range with an axicon lens", Optics Letters, Optical Society of America, US, vol. 27, No. 4, Feb. 15, 2002 (Feb. 15, 2002), pp. 243-245, XP007906548, ISSN: 0146-9592, DOI: 10.1364/OL.27.000243.
D.A. Atchison and G. Smith, "Chromatic dispersions of the ocular media of human eyes", Vo. 22, No. 1/Jan. 2005/J. Opt. Soc. Am. A., pp. 29-37.
Martin Hacker and Michael Kempe, "Tief in die Augen geschaut", Uberblick, Physik Journal 8 (2009) Nr. 2, pp. 31-36.
Abhishek Kumar et al., "Subaperture correlation based digital adaptive optics for full field optical coherence tomography", May 6, 2013, vol. 21, No. 9, Optics Express, 17 pages.
Jason Porter et al., "Monochromatic aberrations of the human eye in a large population", vol. 18, No. 8, Aug. 2001, J. Opt. Soc. Am. A, pp. 1793-1803.

* cited by examiner

OPTICAL COHERENCE TOMOGRAPHY FOR PERFORMING MEASUREMENTS ON THE RETINA

RELATED APPLICATIONS

The present application is a National Phase entry of PCT Application No. PCT/EP2015/073326, filed Oct. 9, 2015, which claims priority from DE Patent Application No. 10 2014 115 157.7, filed Oct. 17, 2014, both of said applications being hereby incorporated by reference herein in their entirety.

FIELD OF THE INVENTION

The invention relates to an optical coherence tomograph for examining an eye, which comprises an illuminating device for providing source radiation of sweepable wavelength, an illumination and measurement beam path, which has a dividing element for dividing the source radiation into illumination radiation and reference radiation, illuminates an illumination field in the eye with the illumination radiation and collects illumination radiation scattered back from the eye as measurement radiation, wherein the illumination and measurement beam path comprises a scanner for adjusting the lateral position of the illumination field in the eye and a front optical system, a reference beam path which guides reference radiation, a detection beam path, which receives the measurement radiation from the illumination and measurement beam path and the reference radiation from the reference beam path and guides them in a superimposed manner onto at least one 2D detector.

The invention further relates to a method for optical coherence tomography for examining an eye, wherein source radiation is provided and swept in respect of its wavelength and divided into illumination radiation and reference radiation, an illumination field in the eye is illuminated with the illumination radiation, illumination radiation scattered back from the eye is collected as measurement radiation, wherein the lateral position of the illumination field in the eye is adjusted with a scanner, the reference radiation is delayed in a reference beam path and superimposed with the measurement radiation in order to generate an interference signal which is detected with a 2D detector.

BACKGROUND

In the field of ophthalmology, optical coherence tomography (OCT) is an established method for imaging the eye. It allows a three-dimensional imaging, which is very useful in the diagnosis of eye diseases and their progression. Here, diseases of the retina are in particular to be mentioned, such as glaucoma or age-related macular degeneration. In OCT systems, the lateral resolution (x and y) is defined by the numerical aperture (NA) of the optical system used. However, the axial resolution (z) is calculated from an interference pattern and, as a rule, is a great deal larger than the depth of field of the image, which in turn depends on the numerical aperture and more precisely is proportional to $1/NA^2$. In usual Fourier domain OCT, which utilizes a broadband radiation source or one in which the wavelength can be adjusted, the depth resolution is inversely proportional to the spectral bandwidth and more precisely is proportional to $\lambda^2/\Delta\lambda$, wherein $\lambda$ is the central wavelength and $\Delta\lambda$ is the bandwidth.

To measure the retina of the human eye, both a high lateral and a high axial resolution are required. At the same time, the detectable and thus illuminated volume at depth (along the optical axis) should be as large as possible; this requires a small numerical aperture (NA) of the optical system. The lateral resolution requires a large numerical aperture. Thus, in the state of the art, ultimately the extent of the accessible depth range and the lateral resolution are linked to each other via the numerical aperture of the optical system and cannot be set independently of each other.

From US 2014/0028974 A1 an OCT based imaging method is known. Here, a line is projected onto an object through an imaging system. Backscattered radiation is combined in an interfering manner with reference radiation and guided to a detector, wherein a confocal filtering is performed in one direction. For this purpose, an astigmatic optical system is used. The depth resolution is defined by optical coherence tomography. In cases of spectroscopic analysis of the radiation, a two-dimensional detector is used, one dimension of which serves for the confocal filtering with respect to the illuminated linear area and the other dimension of which resolves the spectral information. The approach according to US 2014/0028974 A1 also links lateral resolution and accessible depth range.

US 2007/0013918 A1, US 2006/0109477 A1, and US 2007/0238955 A1 describe OCT systems.

In the case of a scanning OCT system, the pupil of the eye is usually accessible in a diameter between 1 mm and 1.5 mm. From this results a lateral resolution of about 15 μm and an accessible depth range of 3 mm. At higher numerical apertures of the optical system a better lateral resolution would be obtained. However, increasing the numerical aperture would reduce the accessible depth range. Moreover, aberrations increase with the numerical aperture. Although, in the case of known OCT systems, which use diameters up to 1.5 mm in the pupil of the eye, aberrations in form of defocusing can usually be disregarded whereas astigmatism and coma increase for larger pupils. Therefore, diffraction-limited resolution cannot be achieved.

For particular applications, in particular for the diagnosis of age-related macular degeneration, a high lateral resolution is desired. To detect the early stages of this disease requires a lateral resolution of about 5 μm. At the same time, a scannable depth range of measurement of about 3 mm is required since it is assumed that age-related macular degeneration is accompanied by the formation of blood vessels in deeper layers of tissue. In order to detect such vessels, a good signal-to-noise ratio is required, too.

SUMMARY OF THE INVENTION

Example embodiments of the invention provide an optical coherence tomograph for performing measurements on the retina of the human eye, in which the lateral resolution is improved without restricting the accessible depth range at the same time.

Example embodiments of the invention combine several features in order to obtain by application of optical coherence tomography a three-dimensional image, which has a particularly good resolution laterally, i.e. transverse to the optical axis, and at the same time can cover a very large depth range axially, i.e. along the optical axis, without an adjustment of focusing elements or lenses having to take place during the measuring procedure.

For this purpose, a 2D detector, is used, which detects a part of the retina. A diaphragm in an intermediate image of the optical imaging defines this part, and the 2D detector is matched to the size of the diaphragm. The beam path is formed such that illumination by illumination radiation and collection of backscattered measurement radiation (detection) can take place with different numerical apertures. Thus, e.g., a smaller numerical aperture can be set for illumination, which consequently illuminates a large axial range, such that the measurement radiation contributing to the interference originates from an extended depth range and consequently, by the OCT principle, an image is obtained over such large depth range. The numerical aperture of collecting the measurement radiation, that is the imaging of an object area, is now to be set independently of the numerical aperture of the illumination, e.g. larger. This combines a high lateral resolution with an extended depth range of illumination that contributes to interference.

The 2D detector is for example a two-dimensional detector. The number of pixels is between 4 and 100 pixels per direction, for example between 5 pixels and 40 pixels. This number of pixels proves to be advantageous for sensing the image both with respect to resolution and also with respect to signal-to-noise ratio and possible image error corrections.

Of particular importance in image error correction are aberrations generated by the eye. Since the numerical apertures of illumination and detection got decoupled, it is possible to carry out the detection, i.e. the imaging of an object area on the retina, with a very high numerical aperture, which is so large that aberrations of the eye play a noticeable role. The spatial resolution of the 2D detector allows, as will be explained later, correction of aberrations when the 2D detector is arranged in a conjugate pupil plane of the imaging. If the 2D detector does not lie in a pupil plane, correction of aberrations is equally possible if the detected signal is converted to be from a pupil plane, as is known in the state of the art for holograms.

In the object plane and in the image planes of a beam path, the image information is pure location information. Imaged structures are recovered as intensity differences also in intermediate image planes. In pupil planes, the image information is pure angle information. The angles of the incident beams encode the image information. This has the known effect, that a change in the cross section of a pupil influences exclusively the image brightness but not the image size. For this reason, the human iris lies in the pupil plane such that the human eye adapts itself with respect to the brightness through constriction or expansion of the iris. So far as, in this description, the plane of the pupil of the eye is discussed, the iris plane is meant. An imaging beam path images an object from the object plane onto an image in the image plane (e.g. the location of a detector). Between, for example, the object plane and an intermediate image plane, there always exists a pupil because of the laws of imaging. Just as there is always an intermediate image plane between two pupil planes. Likewise, in this description, pupil planes which are located between the plane of the pupil of the eye and the detector are referred to as conjugate pupil planes since, predetermined by the optically imaging elements, they are conjugate to the plane of the pupil of the eye. So far as the retina is named here as object, this is not intended to restrict the invention. Other structures of the eye can also be an object for imaging.

Features described in the following for optical coherence tomography can be used for different embodiments either alone or in different combinations. So far as following embodiments relate to particular combinations of features, the invention is not restricted to such combinations.

Embodiments of the invention combine the advantages of a confocal, scanning system with the advantages of a spatially resolving detector. The confocal principle of a scanning system lies in the fact that scattered radiation is very effectively suppressed, resulting in a measurement signal of high signal-to-noise ratio. By enlarging the aperture at the eye, the lateral resolution can be increased at the same time. The invention provides that the numerical aperture of illumination is decoupled from the numerical aperture of detection. Thereby, a high lateral resolution is possible, without impairing the detectable depth range. Design objectives opposing in the state of the art (high lateral resolution requires large NA, large detectable depth range requires small NA) are thus resolved.

Some embodiments of the invention use a confocal diaphragm. In this description, the term "confocal" refers not only to a diaphragm which lies exactly in an (intermediate image) plane conjugate to the object plane, but also covers an arrangement of the diaphragm within a certain range of error in front of or behind an intermediate image plane. If the confocal diaphragm does not lie exactly in the intermediate image plane but near to the intermediate image plane, the function as confocal diaphragm, which defines the object field, from which the measurement radiation is collected, is, however, likewise fulfilled, although the suppression of scattered light is possibly reduced. The diaphragm is considered to be in or near to an intermediate image plane as long as it is spaced apart from the intermediate image plane by at most three times the depth of focus; for example a maximum spacing of not more than one single depth of focus. The depth of focus defines an axial range in the image space, i.e. at the intermediate image plane of an optical system, in which a sufficiently sharp image forms in the image plane. In the range of the depth of focus, diffraction spots are registered as a dot. The range in the object space conjugate to the depth of focus is the depth of field. The depth of field is a measure of the extent of the sharp range in the object space and is given by $\lambda/(NAo)^2$, wherein NAo refers to the numerical aperture in the object space. The depth of focus at the intermediate image plane results analogously to the depth of field from the numerical aperture through $\lambda/(NAz)^2$; here, NAz is the numerical aperture at the intermediate image plane, which is calculated e.g. from NAo by use of the magnification factor. In the above situation, the maximum wavelength of the measurement radiation at the intermediate image plane can be used as wavelength.

It is understood that the features named above and those yet to be explained below can be used not only in the stated combinations but also in other combinations or alone, without departing from the spirit and scope of the present invention.

BRIEF DESCRIPTION OF THE DRAWINGS

The invention is explained in yet more detail below by way of example with reference to the attached drawings, which also disclose features of example embodiments of the invention. There are shown in.

DETAILED DESCRIPTION

Figure 1:
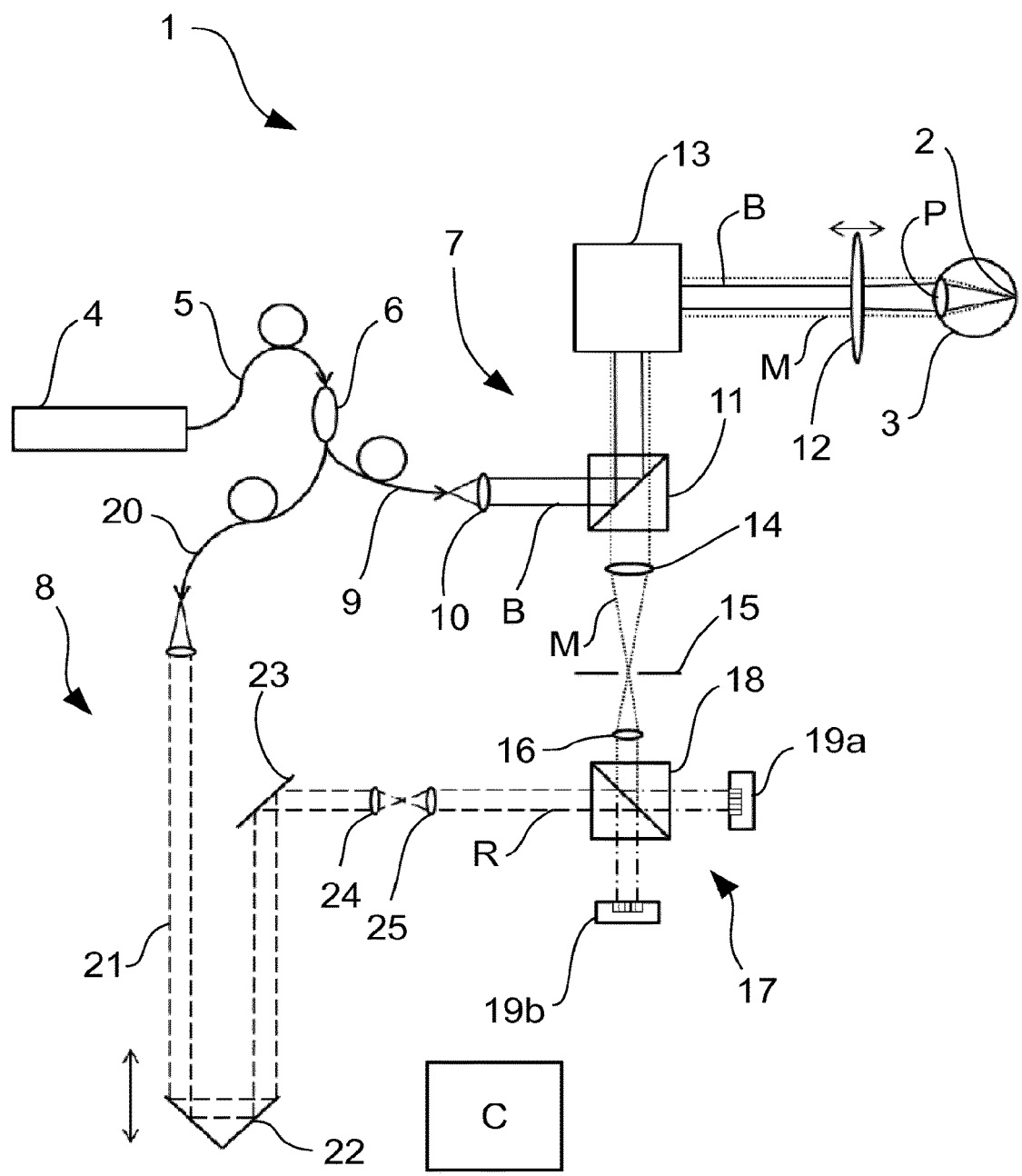
FIG. 1 a schematic representation of an optical coherence tomograph (OCT) in a first example embodiment, FIG. 2 a schematic representation of an OCT in a second example embodiment, FIG. 3 a schematic representation of an OCT in a third example embodiment, FIG. 4 representations to illustrate the correction of an aberration which can be used in one of the OCTs of FIGS. 1 to 3, FIG. 5 a top view of a detector which can be used in any of the OCTs of FIGS. 1 to 3, FIG. 6 a representation to illustrate a depth correction which can be used in any of the OCTs of FIGS. 1 to 3, FIG. 7 signal intensities of different channels of a detector of an OCT according to any of FIGS. 1 to 3, FIG. 8 a representation similar to FIG. 7, FIG. 9 a schematic representation to illustrate the scanning principle in an OCT according to any of FIGS. 1 to 3, and FIGS. 10 and 11 schematic representations similar to FIG. 9 to illustrate the generation of a three-dimensional image.

FIG. 1 depicts an OCT 1, which captures three-dimensional images of a retina 2 of an eye 3. Source radiation of a radiation source 4 which can be tuned with respect to its wavelength, for example a suitable laser, is coupled into a fibre 5. The source radiation is, for example, in the infrared wavelength range. In the following description, this wavelength range is also referred to as "light". Under this term, all radiation of the electromagnetic spectrum which satisfies the optical laws is subsumed.

The fibre 5 terminates into a splitter 6, which splits the source radiation into a measurement arm 7 and a reference arm 8. At the splitter 6, in the measurement arm 7, a fibre 9 is attached, and the illumination radiation B emerging at the end of the fibre is conducted to a beam splitter 11 by an illumination optical system 10. From there, it reaches a front optical system 12, which bundles the illumination radiation B in a focus, which lies on the retina 2 of the eye 3. The illumination optical system 10 and the front optical system 12 thus set, among other things, the numerical aperture NA with which the eye 3 is illuminated. Between the beam splitter 11 and the front optical system 12 there is located a scanner 13, which shifts the focus over the retina 2 biaxial and perpendicular to the direction of incidence, i.e. lateral. The coordinates of such deflection are labelled x and y in the following. The z position of the focus can be set by adjusting the front optical system 12. This is indicated schematically by a double arrow.

The illumination radiation in the illumination focus on the retina 2 is scattered back from different depths z within the depth of field. This depth of field depends from the numerical aperture NA, which is defined by the combination of front optical system 12 and illumination optical system 10 as well as the optical properties of the eye 3.

The backscattered radiation is collected by the front optical system 12 as measurement radiation M. For differentiation of the incident illumination radiation and the backscattered measurement radiation M collected by the front optical system 12, these are plotted differently in FIG. 1. The illumination radiation is drawn in the figure with continuous lines; the measurement radiation M with dotted lines. The measurement radiation collected by the front optical system 12 is guided to the scanner 13. Here, it is descanned with the result that, following the scanner 13, the measurement radiation M is present as a resting beam.

The collection of the measurement radiation M is an imaging of the retina 2. The beam splitter 11 separates the measurement radiation M from the illumination radiation B and guides it to detector optical system 14. The detector optical system 14 defines, together with the front optical system 12 and the optical properties of the eye 3 as well as any further imaging elements in the imaging beam path (e.g. a lens 16), the numerical aperture NA of the imaging of the retina 2. In this way, illumination and detection have different numerical apertures. The numerical aperture of the illumination is defined by the combination of the illumination optical system 10 and the front optical system 12. The numerical aperture of the detection is defined by the detector optical system 14 and the front optical system 12.

The detector optical system 14 focuses the measurement radiation M to an intermediate image plane, in which a diaphragm 15 is located. This diaphragm 15 defines the size of the object field in which measurement radiation M is detected from the retina 2. Taking into consideration the magnification factor of detector optical system 14, front optical system 12 and eye 3, the size of the diaphragm 15 corresponds exactly to the size of the object field on the retina 2, from which measurement radiation M is collected.

A further optical system 16 following the diaphragm 15 directs the measurement radiation M onto a detector device 17. In the embodiment of FIG. 1, the detector device 17 comprises a beam splitter/combiner 18 as well as two 2D sensors 19a and 19b. The size of the 2D sensors 19a, 19b is designed to match the diaphragm 15 and the intermediary optical system 16. They have a spatial resolution, i.e. they resolve an intensity distribution over beam cross section. The detector device 17 for example lies in a pupil plane of the measurement beam path, i.e. in a plane which is conjugate to the plane of the pupil P of the eye 3, through which the measurement radiation M emerges.

At the beam splitter/combiner 18, reference radiation R from the reference arm 8 is also coupled in. Following the splitter 6, the reference arm comprises a fibre 20. In the embodiment shown in FIG. 1, the reference arm 8 has a path length adjusting device 21, which serves to set the length of the reference arm 8 to match the position of the retina 2 of the eye 3. For this purpose, the radiation is coupled out of the fibre 20 and conducted via a retroreflector 22, the position of which can be adjusted, as the double arrow in FIG. 1 indicates. Via a further deflecting mirror 23 as well as optical systems 24, 25, the reference radiation R is conducted to the beam splitter/combiner 18, which conducts the reference radiation R with the measurement radiation M in a superposed manner onto the area sensors 19a and 19b.

In FIG. 1, the path length adjusting device 21 is designed as a free beam path. This is optional, as is the use of a retroreflector 22. In the state of the art, various measures are known for adjusting the optical length of a beam path.

In FIG. 1, the detector device 17 is designed for so-called "balanced detection". This is also optional, as is further explained in the following with reference to FIG. 2. Balanced detection has the advantage that a common mode portion in the superposition of reference radiation R and measurement radiation M can be suppressed in a particularly simple manner. Alternatively, such a suppression could be dispensed with if only one of the detectors, for example the detector 19b, was used and the beam splitter/combiner 18 is designed as a simple beam combiner.

The signal of interference between reference radiation R and measurement radiation M is converted to an image, as is known for optical coherence tomography. Since the wavelength of the source radiation is tuned, the Fourier domain principle of image generation is utilized, which is generally known from the state of the art.

For image generation, the OCT 1 comprises a control device C, which receives a wavelength tuning signal and the measurement signals of the 2D detectors 19a, 19b. Optionally, the control device C controls the radiation source 4 for wavelength tuning, therefore knows the wavelength currently prevailing in the system and can thus assign the measurement signals accordingly. The 2D detectors receive measurement radiation M from an object field on the retina 2, which is defined by the diaphragm 15. The size of the 2D detectors 19a, 19b is adapted to correspond to the diaphragm 15 and they sense the intensity distribution in a spatially resolved manner with their individual pixels. If the 2D detectors 19a, 19b lie in an image plane, i.e. in a plane which is conjugate to the plane of the retina in the imaging process carried out by front optical system 12, detector optical system 14, and further intermediary optical elements, the individual pixels already contain the location information from the object field. If, on the other hand, the 2D detectors lie in a conjugate pupil plane, which is conjugate to the plane in which the pupil P of the eye 3 lies, the detectors detect the intensity distribution in the pupil plane and thus the phase information. This can also be used for image reconstruction, as will be explained later.

It is important for the invention that the scanner 13 shifts the object field over the retina 2 since it acts not only on the illumination radiation B but also on the collection of the measurement radiation M. At each position of the scanner 13, a single image of the retina forms, the resolution of which is determined by the number of pixels and the arrangement of the 2D detectors 19a, 19b. As will be explained in the following, these single images are assembled to form a total image, which has a considerably higher resolution than known from standard widefield OCT.

In the design of FIG. 1, the beam splitter/combiner 18 combines the measurement radiation M from the measurement arm 7 and the reference radiation R from the reference arm 8. The 2D detectors 19a, 19b detect the pattern of the interference between measurement radiation M and reference radiation R. The requirements necessary to generate such interference, in particular the properties of the radiation source 4 and of the path length adaption, are known in the state of the art of optical coherence tomography. Because of the balanced detection, there is a relative phase difference of pi between the sum of the two signals of the two 2D sensors 19a, 19b.

The complex amplitudes of the measurement radiation and of the reference radiation can be written as:

$$U_{sample} = u_s * e^{i\varphi_s} \text{ and}$$

$$U_{reference} = u_r * e^{i\varphi_r},$$

if the amplitudes are labelled with $u_s$ and $u_r$ and the phases of the signals in the two arms are labelled with $\varphi_s$ and $\varphi_r$ (the indices "sample" and "s" relate to the measurement arm, the indices "reference" and "r" relate to the reference arm).

The signals $I_1$ and $I_2$ detected by the two sensors 19a, 19b are then:

$$I_2 = |U_{sample} + U_{reference}|^2 = |U_{sample}|^2 + |U_{reference}|^2 + 2Re\{U_{sample} * \overline{U}_{reference}\} \text{ and}$$

$$I_2 = |U_{sample} + U_{reference} * e^{i\pi}|^2 = |U_{sample}|^2 + |U_{reference}|^2 + 2Re\{U_{sample} * \overline{U}_{reference} * e^{-i\pi}\}.$$

$\overline{U}$ is complexly conjugate to U, and Re is an operator, which supplies the real part of a complex value. As differential signal $I_{bd}$ of the two detectors 19a, 19b, the following is obtained:

$$I_{bd} := I_1 - I_2$$
$$= 2Re\{U_{sample} * \overline{U}_{reference}\} - 2Re\{U_{sample} * \overline{U}_{reference} * e^{-i\pi}\}$$
$$= 2 * u_s * u_r * \cos(\Delta\varphi) - 2 * u_s * u_r * \cos(\Delta\varphi - \pi)$$
$$= 4 * u_s * u_r * \cos(\Delta\varphi)$$

wherein $\Delta\varphi := \varphi_s - \varphi_r$ refers to the relative phase between measurement and reference arm.

The formulae show that only the interference pattern of the two signals $\cos(\Delta\varphi)$ is still present in the differential signal of the two detectors 19a, 19b and the common mode components $|U_{sample}|^2$ and $|U_{reference}|^2$ are suppressed.

In this way, in particular in the case of any subsequent analog-digital conversion of the differential signal, the dynamic range of the signal is used to the maximum for information extraction.

Another embodiment works without balanced detection; the signal amplitude of the interference signal is then modulated onto a common mode portion and is filtered out by suitable data analysis.

Figure 2:
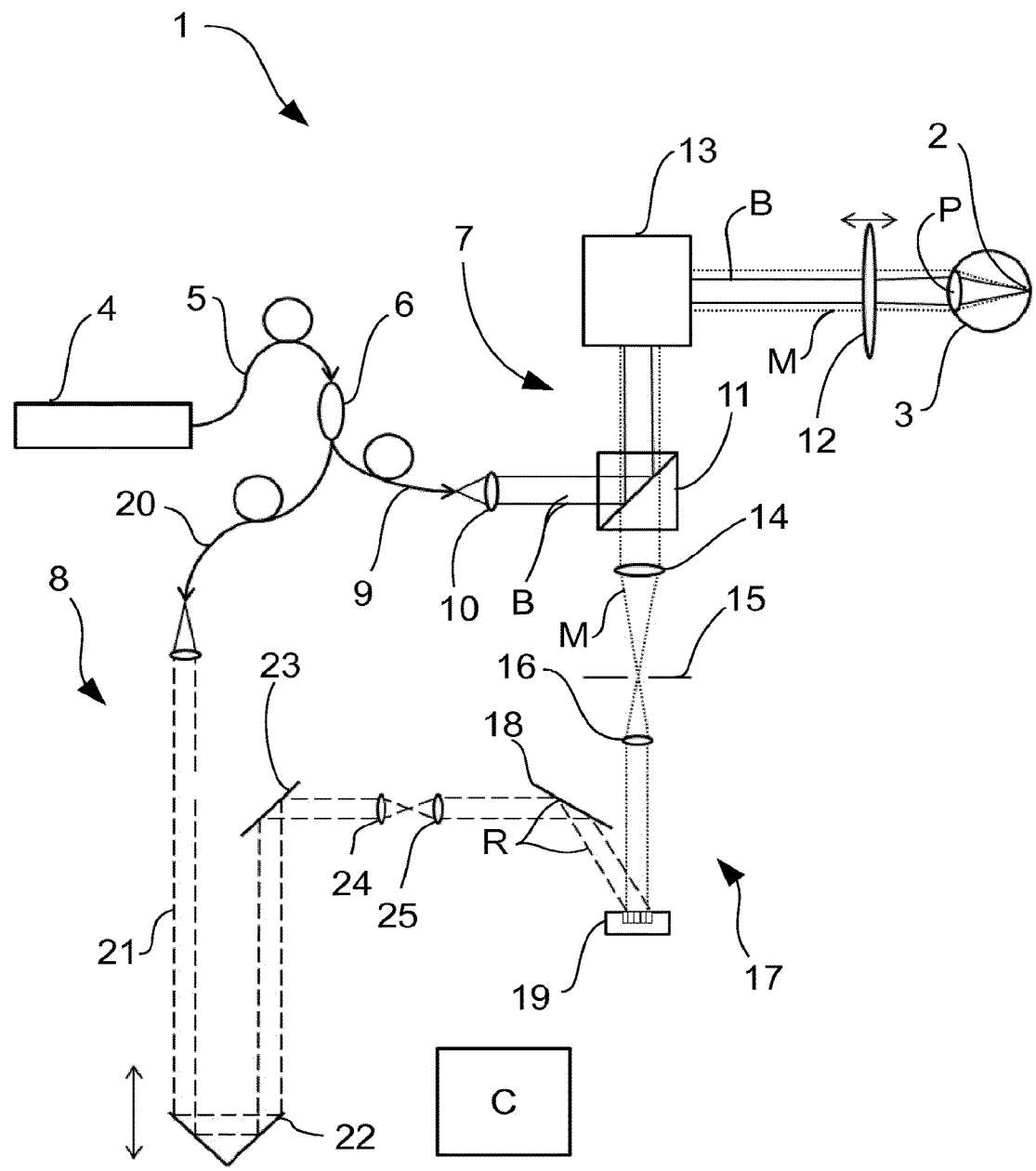

FIG. 2 shows a modified design of the OCT 1, which resembles that of FIG. 1 in many respects. The same elements bear the same reference numbers as in FIG. 1. The essential difference consists in the design of the detector device 17, which, in the design of FIG. 2, comprises only one single 2D detector 19. The measurement radiation M and the reference radiation R strike this 2D detector 19 at an angle and interfere with each other. Through the angular offset, a phase shift occurs between pixels which lie in a plane which is spanned by the optical axis, along which the measurement radiation M is incident, and by the optical axis, along which the reference radiation R is incident. This phase shift can be evaluated to suppress the common mode portion. Such a detection arrangement is referred to as off-axis detection and is known for common mode suppression to a person skilled in the art.

Figure 3:
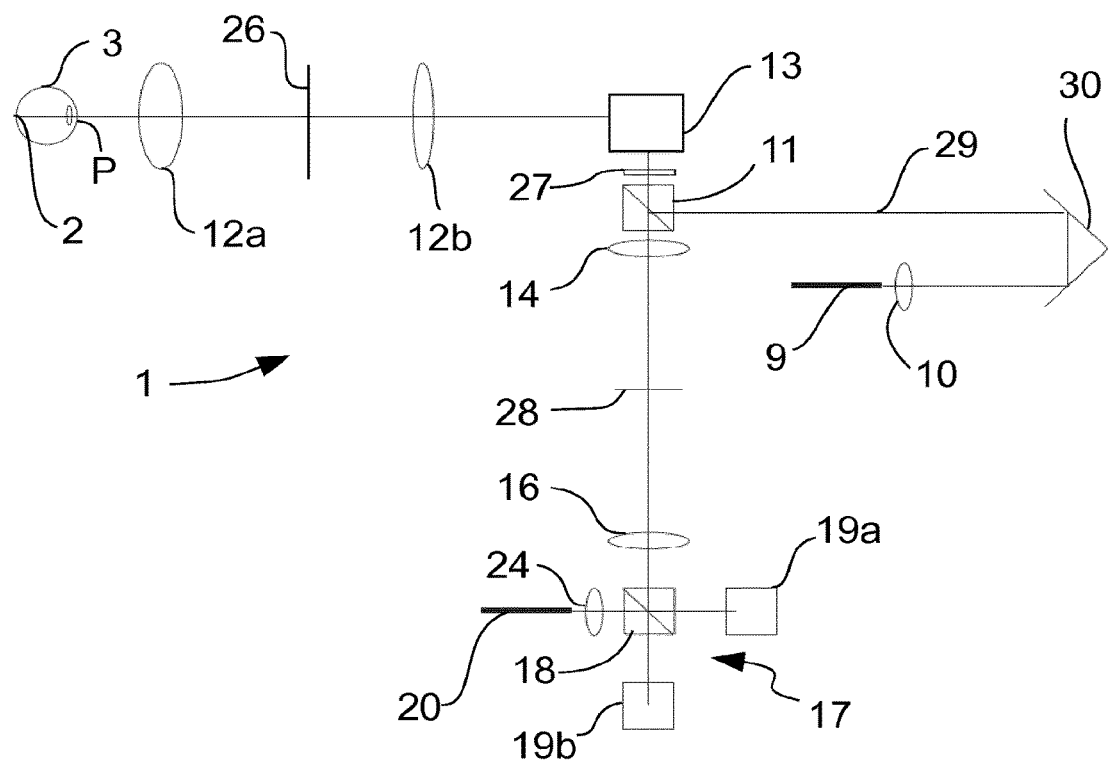

FIG. 3 shows a further embodiment for the OCT 1, wherein here the path length adjusting device is not arranged in the reference arm 8, but in the measurement arm 7. Following the fibre 9 and the illumination optical system 10 there is a path length adjusting device 29, again purely by way of example in form of a movable retroreflector 30. The embodiment of FIG. 3 shows that it does not matter whether the path length adjusting device lies in the reference arm 8 or in the measurement arm 7. It is also possible to provide a path length adjusting device in both of them. It is only necessary that the interference state between the reference radiation R from the reference arm 8 and the measurement radiation M can be set such that it is adapted to the current measuring task, i.e. the actual position of the object to be measured, in the embodiment examples described here by way of example the retina 2 of the eye 3.

In FIG. 3, two further features are represented which can be used individually for all embodiments of the OCT 1. The front optical system 12 is formed in two parts by two imaging elements 12a and 12b.

The scanner 13 is for example located, in the case of the OCT 1 of FIGS. 1 to 3, in or near to a pupil plane of the detection beam path as well as also of the illumination beam path. This pupil plane is conjugate to the plane of the pupil P of the eye 3.

The front optical system 12 comprises the optical sub-systems 12a and 12b, which together form a 4f optical system. Thus, the optical sub-system 12a is an ophthalmoscopic lens and the optical sub-system 12b is a scan lens. This 4f optical system images the pupil P of the eye 3 to a pupil plane conjugate to the plane of the pupil P, in which pupil plane the scanner 13 lies. The scanner 13 does not have to be placed exactly in this conjugate pupil plane but that does have advantages. Between the plane of the pupil P of the eye 3 and the pupil plane conjugate thereto there is an intermediate image plane 26. Because of its proximity to the scanner 13, the beam splitter 11 is also located near to the conjugate pupil plane. It is also possible to place the beam splitter 11 in this conjugate pupil plane if the scanner 13 is moved out of the conjugate pupil plane.

In one embodiment, the beam splitter 11 is formed as a polarizing splitter. Then, a lambda/4 plate 27 is arranged in front of it when seen in imaging direction. This embodiment will be discussed later.

The detector optical system is likewise formed as a 4*f* optical system. It provides a further intermediate image plane 28, in which lies the diaphragm 15 (not drawn in in FIG. 3). The intermediate image plane 28 is conjugate to the object plane, in which lies the retina 2 to be imaged. The size of the diaphragm 15 (not shown) determines the size of the imaged area on the retina 2, of course under consideration of the magnification factor which is relevant to the generation of the intermediate image plane 28.

In all embodiments, the diaphragm 15 has two functions. On the one hand, it suppresses scattered light, whereby the contrast is improved at the detector device 17. Ultimately, in this respect the diaphragm acts in a similar way to a confocal diaphragm of confocal scanning OCTs. Because of the effect of the detector optical system, the detector device 17 for example lies in a plane which is conjugate to the pupil plane of the eye, or near to this plane. This arrangement is advantageous but not mandatory. It has the advantage that the phase function of the electromagnetic field can be sensed easily. The maximum spatial frequency in the plane of the 2D detector 19 or of the 2D detectors 19*a*, 19*b* is predetermined by the size of the object field on the retina 2 and thus, ultimately, the size of the diaphragm 15 in the intermediate image plane 28. The diaphragm 15 thus, on the other hand, facilitates a particularly favourable signal detection.

Figure 5:
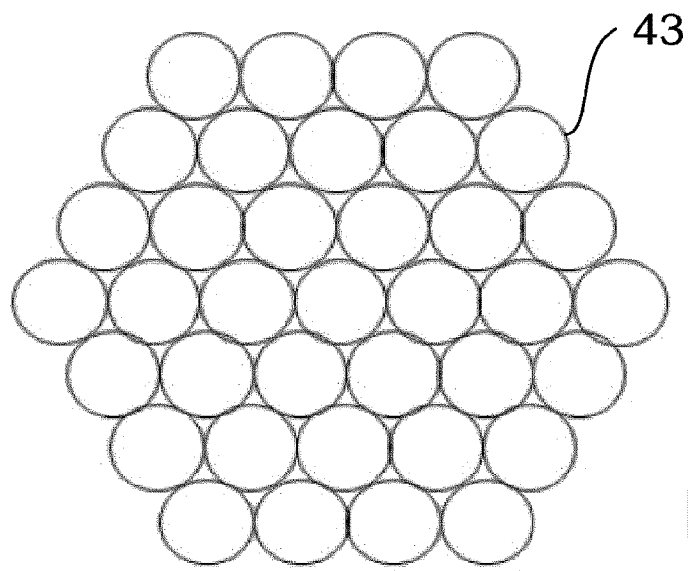

In all embodiments of the OCT, the number of pixels of the 2D detector is 4 to 100, for example 5 to 50, in another example 5 to 40 pixels in each direction. FIG. 5 shows a top view 43 of the detector in that the arrangement of the pixels does not necessarily have to be rectangular but that a hexagonal arrangement of the pixels is also an option. The pixel pattern can be chosen freely, thus.

In the state of the art, holoscopic OCT systems are known which comprise detectors with 100 to 4000 pixels per direction. These numbers of pixels are deliberately not used here. The number of pixels is linked to the required illumination brightness, the measurement rate and the suppression of multiple scatterings.

In an example embodiment of the OCT 1, aberrations are corrected. The detector device 19 comprises, as already mentioned, one or two 2D detectors which have a spatial resolution in the form of pixels. These pixels are also referred to as channels in the following. The measurement signal is distributed over these several channels of the detector(s). If, in an example embodiment, the detector lies in a conjugate pupil plane, each channel of the detector receives measurement radiation M from different angles, which radiation was scattered from the retina 2. The spatial resolution of the 2D detector 19, 19*a*, 19*b* allows it to detect the distribution of the measurement radiation in the pupil P. Aberrations have an effect on this distribution. Aberrations caused by the eye 3 often assume a level which is no longer acceptable when an area in the plane of the pupil P of the eye 3 is utilized, which is larger than 1.5 mm in diameter. However, such a larger area would be desirable with respect to the lateral resolution. Without spatial resolution in the conjugate pupil plane, a larger pupil utilization in the eye 3 would mix and average phase differences in the then single detection channel.

Figure 4:
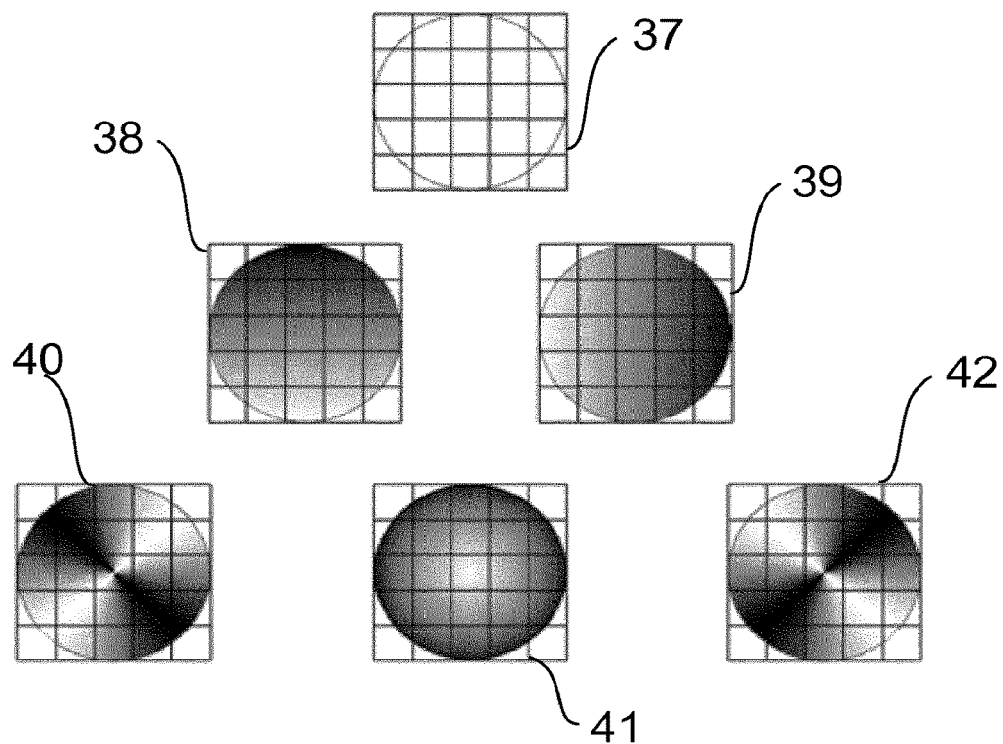

The corresponding Zernike polynomials which describe these aberrations are represented in FIG. 4, which shows top views 37 to 42 of a conjugate pupil plane. Further, the grid of a detector with 5×5 channels (or pixels) is shown. The pixels sense the pupil P and thus allow phase differences within the pupil P to be distinguished.

The maximum resolvable phase differences depend on the number of channels. It was found that the number of distinguishable phase differences in this plane results from the number of channels per direction multiplied by pi. In the case of five channels per direction, as is represented in FIG. 4, polynomials to $Z''_4$ can be distinguished, wherein m can assume the values 0 (sphere), ±2 and ±4. This applies to channels with an infinitesimally small surface area. In reality, of course, they have a particular size. The measurement signal detected in a channel therefore corresponds to an averaging of the interference signal over the surface area of the respective channel (pixel area). The maximum theoretically possible order of the Zernike polynomial can thus only be achieved when the phase of the signal within a channel varies by less than pi. It was found that, at an average wavelength of the OCT of 1060 nm, with uniformly spatially distributed channels, the phase differences of astigmatism caused by the eye can be detected, if, in the case of five channels, the condition 2 pi/(5 channels per aberration period)≤pi is met. Then, a period of minima and maxima lies within the aperture. For higher orders, the following applies: 0.6*2 pi/(5 channels per period of the aberration)=1.2*pi/(5/1.5)≤pi for the third order and 0.5*2 pi/(5 channels per period of the aberration)=1.0*pi/(5/2)≤pi for the fourth order.

These findings show that a 2D detector with at least five channels per direction is capable of resolving at least astigmatism and the aberrations of third order. A higher number of channels allows even higher orders of the aberration to be detected.

The above analysis considered only one spatial direction. As FIG. 4 shows, the aberrations generally have a two-dimensional pattern. In the top view 37, FIG. 4 shows the aberration of first order, which is also referred to as "piston", the top view 38 shows the aberration "tilt", the top view 39 shows the aberration "tip", top view 41 shows the aberration "defocus" and the top views 40 and 42 show aberrations of the "astigmatism" type. As can be seen, most aberrations have a two-dimensionally distributed pattern, whereby the phase variation is also two-dimensional. This pattern can be detected and corrected by the spatially resolving 2D detector 19, 19*a*, 19*b*.

For each detector channel c, the aberrations produce a phase $\theta_c$: $U_{sample,c} = U_{sample} * e^{i\theta_c}$. It results from a thickness δd and a refractive index δn of the passed-through material of the eye (e.g. cornea, aqueous humour, lens, vitreous body), which in reality differs from a theoretical, aberration-free eye:

$$\theta_c(k) = \delta n(k) * k * \delta d_c$$

Thus, the detected signal is shifted by the aberration-dependent phase:

$$I_{bd,c}(k) = 4 * u_s * u_r * \cos(k * \Delta z - \delta n(k) * k * \delta d_c)$$

$$= 4 * u_s * u_r * \cos(k * (\Delta z - \delta n(k) \delta d_c))$$

For monochromatic radiation of 780 nm, the eye causes wavefront aberrations of up to 0.7 nm, which lead to a phase shift of 2*pi (if defocus is disregarded). Such a phase shift corresponds to a deviation in thickness between lens and aqueous humour (these are the elements with the greatest differences in refractive index in the eye), which assumes the following value:

$$\delta d = 2Pi * \frac{780 \text{ nm}}{2Pi * \delta n(780 \text{ nm})} =$$

$$\frac{780 \text{ nm}}{n_{lens}(780 \text{ nm}) - n_{aqueous}(780 \text{ nm})} \approx \frac{780 \text{ nm}}{1.415 - 1.334} \approx 10 \text{ μm}.$$

With known dispersion data, the following results:

$$\theta_c(\lambda_0 = 1060 \text{ nm}) = \frac{2Pi}{1060 \text{ nm}} * (n_{lens}(1060 \text{ nm}) -$$
$$n_{aqueous}(1060 \text{ nm})) * \delta d_c$$
$$= \frac{2Pi}{1060 \text{ nm}} * (1.4104 - 1.3301) * 10 \text{ μm}$$
$$= 1.516 Pi$$

or $$\theta_c(k_0) = k_0 * 0.8034 \text{ μm}.$$

If a wavelength range of $\Delta\lambda = 50$ nm is covered, the phase differences of the associated wave numbers ($k_0 \pm \Delta k$) are:

$$\theta_c(k_0 + \Delta k) = \frac{2Pi}{1110 \text{ nm}} * (n_{lens}(1110 \text{ nm}) -$$
$$n_{aqueous}(1110 \text{ nm})) * \delta d_c$$
$$= \frac{2Pi}{1060 \text{ nm}} * (1.4099 - 1.3297) * 10 \text{ μm}$$
$$= 1.445 Pi$$
$$= (k_0 + \Delta k) * 0.8022 \text{ μm}$$

and $$\theta_c(k_0 - \Delta k) = \frac{2Pi}{1010 \text{ nm}} * (n_{lens}(1010 \text{ nm}) -$$
$$n_{aqueous}(1010 \text{ nm})) * \delta d_c$$
$$= \frac{2Pi}{1060 \text{ nm}} * (1.4098 - 1.3305) * 10 \text{ μm}$$
$$= 1.594 Pi$$
$$= (k_0 - \Delta k) * 0.8048 \text{ μm}.$$

These calculations show that, in sufficiently exact approximation, the phase shifts which are caused by the aberrations vary linearly with the wave number k within a wavelength sweep. The detected measurement signal can thus be expressed as follows:

$$I_{bd,c}(k) = 4 * u_s * u_r * \cos(k*(\Delta z - \delta n(k_0)\delta d_c)).$$

Figure 8:
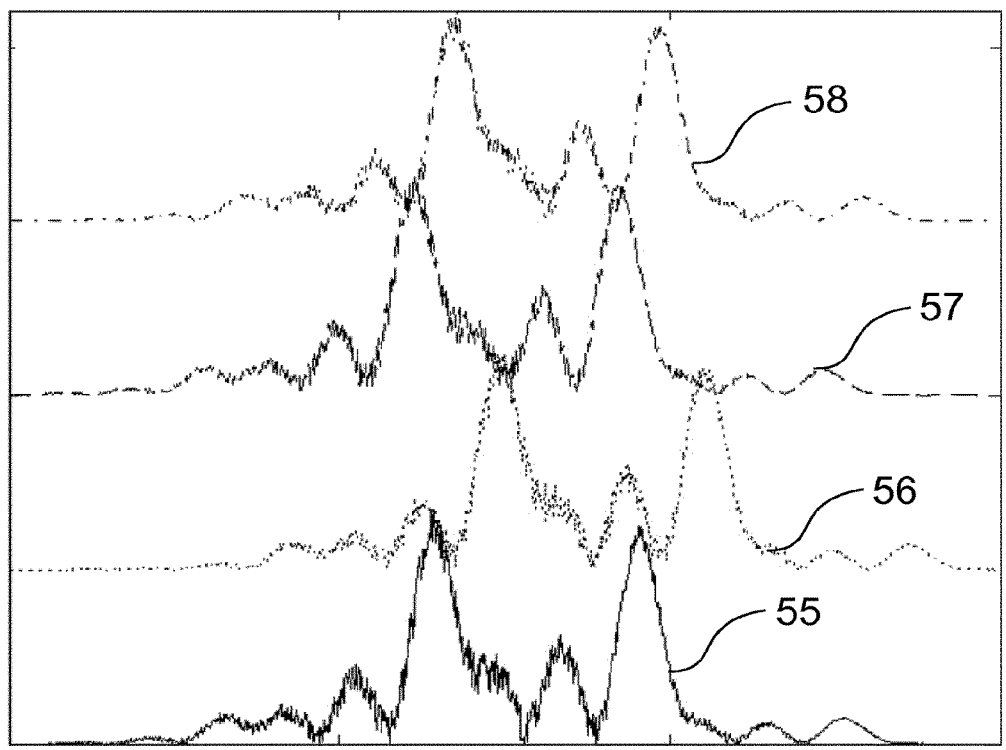

A Fourier transformation for the measured wave numbers k yield the axial distribution, i.e. the distribution of the scattering tissue in z direction. Compared with an aberration-free system, the axial distribution is shifted by the value $\delta n(k_0)\delta d_c$ for each channel c of the 2D detector. FIG. 8 shows a corresponding simulation example, in which the z coordinate is plotted on the x axis and the signal intensity is plotted on the y axis. The curves 51 to 54 correspond to four channels c of the 2D detector. It can be assumed that, in most areas of the tissue, the variation of the axial scatter profile is small within a pupil size of 5 mm of the eye 3. The differences in profile for the channels c are therefore caused mainly by the aberrations, which shift the profile axially. It is therefore provided to relate the aberration-caused phases $\theta_c(k_0)$ of the channels to a central channel (for example the channel lying in the center of the detector, which channel corresponds to a perpendicular incidence on the sample). The measured intensities for a frequency determination are multiplied by the phase factor to correct the aberrations. The phase factor is $e^{-i\theta_c(k_0)}$.

Each channel of the detector has a particular position in relation to the retina 2. The interference signal can be captured during the wavelength adjustment of the laser for the respective wave number $k=2*pi*n/\lambda$, wherein n is the refractive index of the medium and $\lambda$ is the wavelength. As in conventional OCT systems, the measurement signals are Fourier-transformed with respect to the wave numbers, and the depth distribution of the scattering layers is calculated. Here, the relationship $\Delta\varphi = k * \Delta z$ is used, wherein $\Delta z$ is the distance of one scattering layer to a layer, from which the measurement radiation passed through a certain path length to the detector, which certain path length is identical to the path length of the reference radiation.

Figure 6:
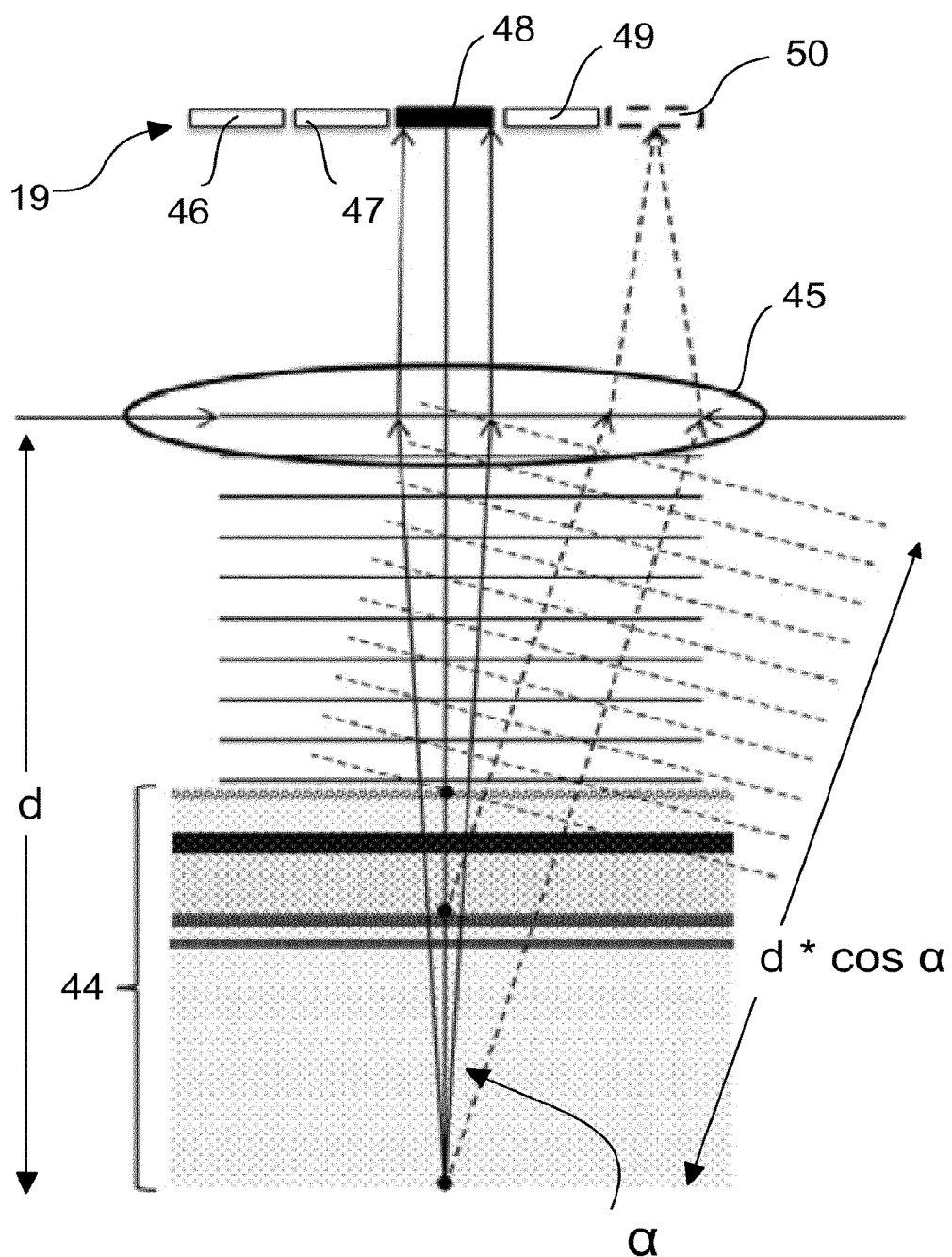
Figure 7:
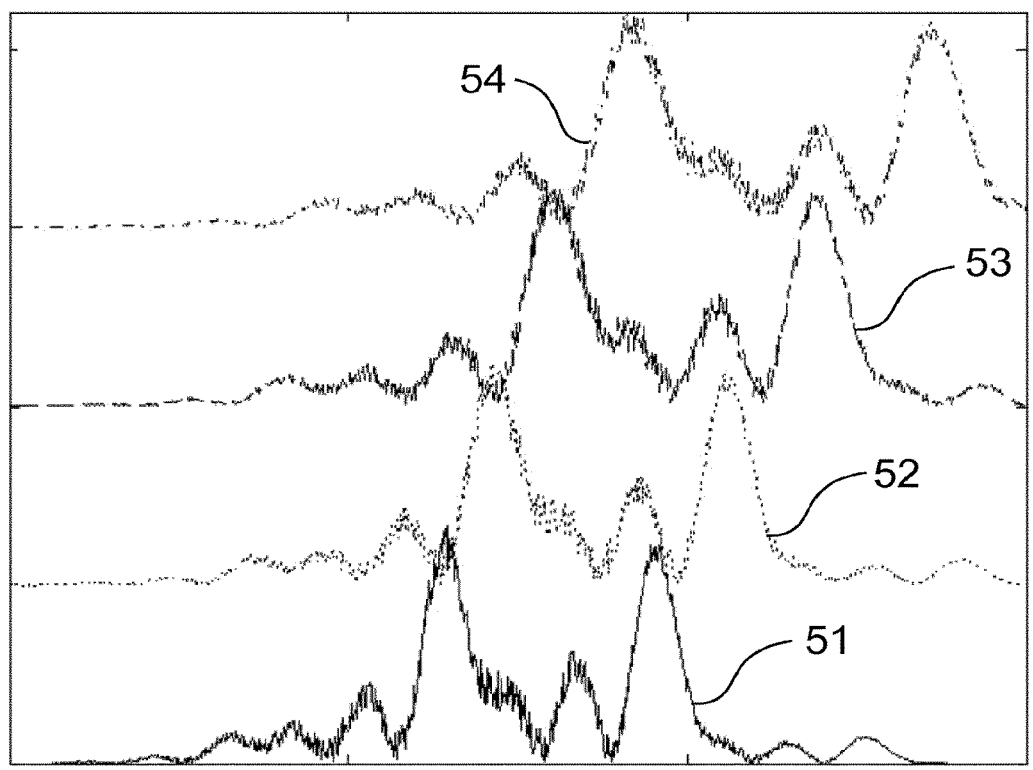

Because of the lateral extension of the 2D detector 19, however, the optical path length for the individual pixels is not identical, as FIG. 6 shows. The five pixels or channels 46, 47, 48, 49 and 50 drawn in by way of example for the 2D detector 19. They differ with respect to the optical path length to a particular point in the tissue 44. The wavefronts for the central channel 48 are drawn in with continuous lines. They are perpendicular to the optical axis of the beam path between the channel 48 and the observed point, which is drawn in at the bottom of the structure 44. For the central channel 48, the radiation runs along the optical axis. For a channel situated further out, for example the channel 50, the chief ray runs at an angle α to the optical axis such that the path length, which has the value d for the central channel 48, takes the value d*cos(α) for the outer channel 50. The corresponding wavefronts and chief rays for the outer channel 50 are drawn in with dashed lines in FIG. 6. Further, in FIG. 6 the lens of the eye 45 is shown by way of example. The depth is based on the principal plane of the lens of the eye since the refractive index step thereof can be used as a reference point during the measurement. As FIG. 6 clearly shows, pixels/channels which lie further out collect radiation which has covered a longer path through the medium. In a reconstruction of the image information, this has the effect shown in FIG. 7 by way of example. There, signal curves 51 to 54 are shown for four channels. The plot corresponds to that of FIG. 8, i.e. the depth coordinate z is plotted on the x axis, the intensity on the y axis. As can be seen, the individual curves are not only shifted in the z direction, they are also concentrated for pixels lying further out. The curve 54 is the measurement signal of the central pixel 48, and the curves 53, 52 and 51 are measurement signals from channels lying further out in each case.

The measurement error caused by this effect is corrected in an example embodiment, in order to obtain a particularly good image capture. The geometric effect is for example corrected by carrying out a rescaling from z to z cos($\alpha_c$), wherein as is the angle which the $c^{th}$ channel has to the optical axis. The angle α is based on a virtual position of the 2D detector 19 in which the detector is placed directly in front of the eye and by taking into consideration the magnification factor. A 2D detector which lies exactly in a plane conjugate to the pupil plane of the eye virtually extends in the plane of the pupil P of the eye 3 at a size which is modified by the magnification factor.

In the reconstruction with respect to the aberration, different channels are reconstructed independently. Subsequently, the cross-correlation is formed in axial direction, i.e. in depth direction, in order to determine the relative phase offsets between the individual channels. A reconstruction of the lateral image for each channel (optionally, as will be described in the following, taking into consideration the scanning procedure) and then of the phase gradient yields a lateral offset in the image which is obtained for a given position of the scanner. This image is also referred to in the following as a pupil channel partial image. By a lateral cross-correlation of the pupil channel partial image an embodiment determines the aberration and, in this way, determines and numerically corrects the entire aberration phase distribution.

The quality of these approaches depends on the sample structure. In case of the human eye, an easily recognizable axial layer structure is available. Lateral thereto, the structures are relatively rough, for example on account of blood vessels or the papilla, combined with very fine structures, such as photoreceptors, wherein few structures lie in between in terms of size and roughness. An example embodiment, therefore, carries out a depth correlation correction by using the axial layer structure in order to correct the greatest proportion of the pupil phase aberrations. Optionally, a lateral correlation correction follows, which utilizes lateral structures, such as for example photoreceptors, which became visible because of the first correction.

The aberrations of the eye are different at different points of the retina. In principle, it is possible to calculate the aberration-caused phase changes in each channel for all points in a lateral image. In a simplified embodiment, it is assumed that the aberrations do not vary very greatly laterally, and the aberrations are calculated only for a few lateral locations of the retina and are interpolated for locations in between.

If a relatively large wavelength range is covered, it is preferred to take into consideration the dispersion of the aberrations. In this embodiment, it is not assumed that the phase shifts change linearly with the wave number k. A peak in the profiles, which originates at the fundus of the eye 3 in the OCT image of the retina 2, is therefore used in order to balance the shift of the profiles with respect to each other. For example therefore, a structure (in the form of a peak) is sought, in the curves 51 to 54 of FIG. 7, and the curves are corrected relative to each other on the basis of this reference structure. In this way, the aberrations $\theta_c(k_0)$ can be determined and corrected as described above. Alternatively, a complex correlation algorithm is also possible, which is applied to the profiles of the different channels. In addition to a shift, a scaling (compression or expansion) of the measurement signals can also be corrected.

In one position of the scanner 13, a single image of the retina is obtained, the size of which is predetermined by the diaphragm 15 and the front optical system 12 and the detector optical system 14 co-operating during the imaging of the measurement light. A Fourier transformation of the signal of the channels provides the image of the sample, but only in a part which corresponds to the size of the detector in the pupil. In order to generate a larger image, the scanner 13 is provided, which shifts the position of the imaged object field, i.e. the image section on the retina 2. The image section corresponds to a single image 59, which has a centre 60. For the current deflection by the scanner 13, it is sufficient for simplification to refer to the centre 60 of the single image 59.

Figure 9:
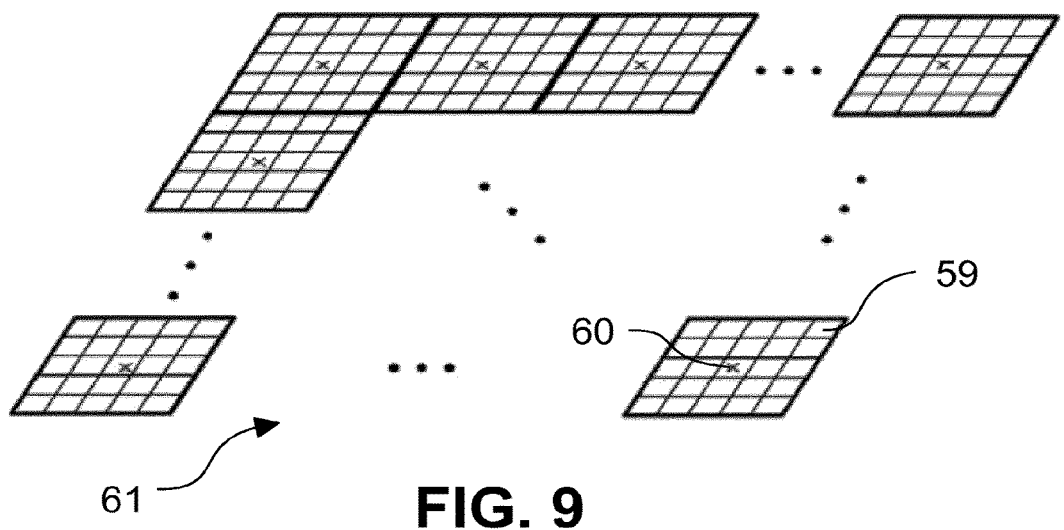
Figure 10:
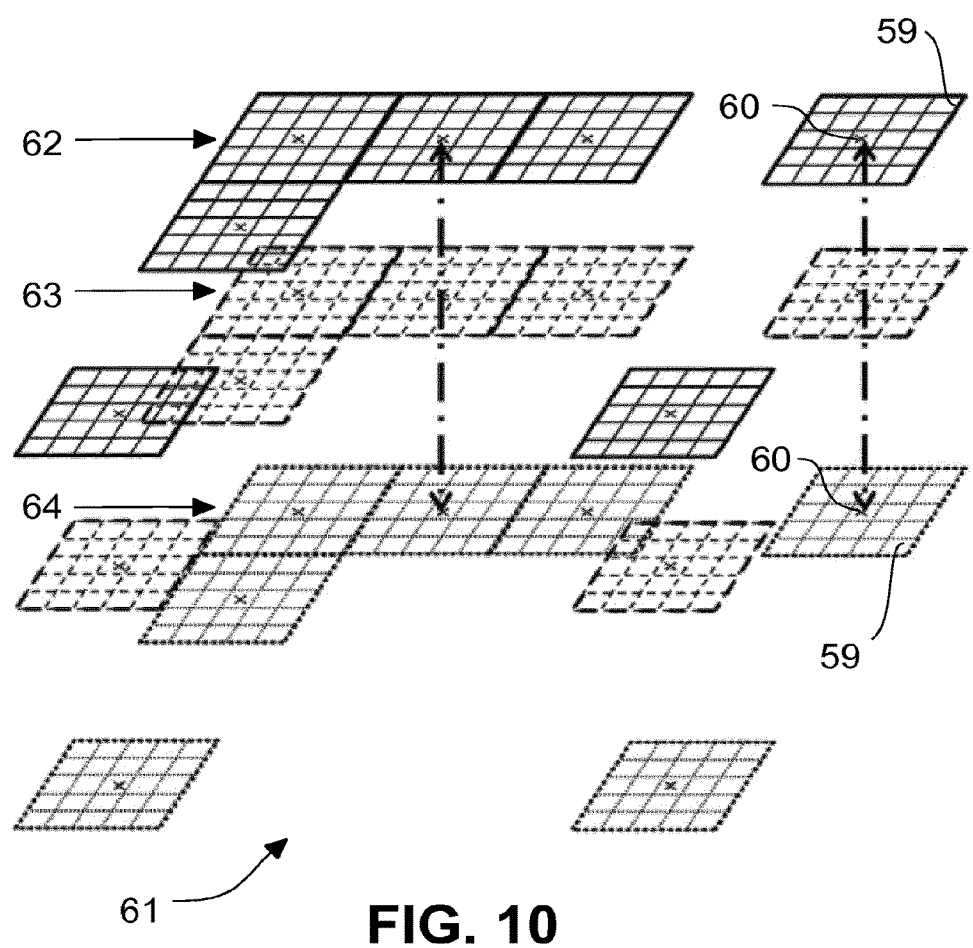
Figure 11:
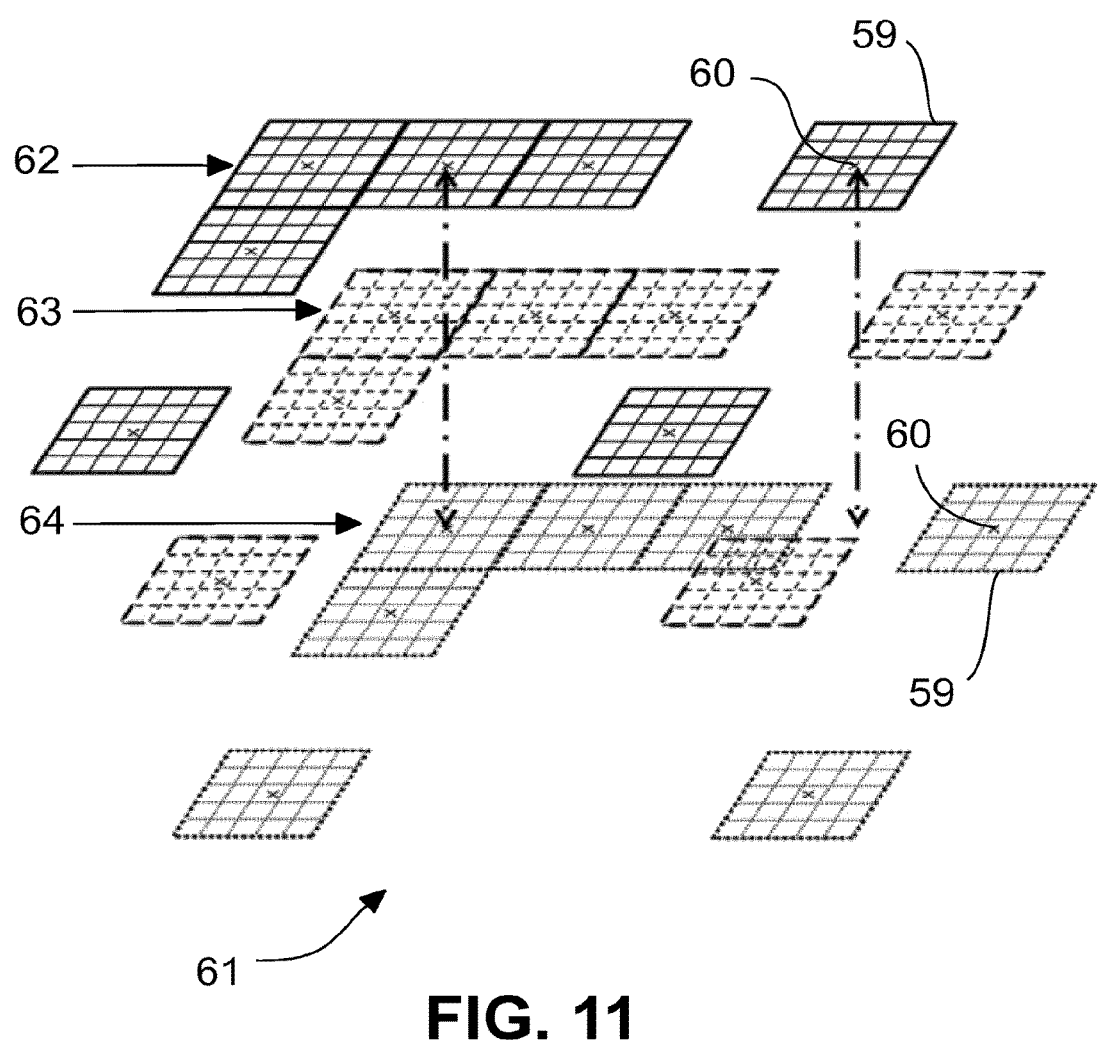

Various scanning approaches are possible now. For instance, the center 60 of the single image 59 can be left unchanged during the sweep of the wavelength of the light source 4. Before a new sweep is started, the center 60 is shifted such that a new single image 59 borders directly on the previously captured single image 59. In this way, a larger total image 61 of the retina can be detected. This approach is shown for a depth plane in FIG. 9. As a result, individual single images 59 are assembled to form the total image 61. The images from the individual planes then result in a three-dimensional image of a cuboid zone in the retina 2. FIG. 10 shows this, in which three planes 62, 63 and 64 can be seen by way of example. The single images 59, which are referenced to each other in the representation of FIG. 10 with a dot-dashed double arrow, in each case originate from one wavelength sweep of the light source 4. Since the scanner 13 rests during each wavelength sweep and is only adjusted between them, the single images 59 generated from one wavelength sweep lie in the planes 62 to 64 all with their centres 60 exactly one above the other.

For particular embodiments of the scanner 13 it is preferred to operate the scanner continuously, i.e. to adjust while the wavelength is adjusted in a sweep. This approach requires synchronization of the scanner 13 and wavelength adjustment at the light source 4. Here, it is preferred to set the lateral adjustment speed through the scanner 13 such that, during one wavelength sweep, at most one single image 59 is passed in one direction, preferably even fewer. Thereby, for the individual planes 62, 63 and 64, the position of the centers 60 changes since the single images 59 in the planes come from different wavelengths of the Fourier transformation. As a result, a temporary total image 61 is obtained, which, unlike in the embodiment of FIG. 10, is not a right-angled cuboid, but is e.g. a no longer right-angled parallelepiped, depending on the adjustment of the scanner 13 during the wavelength sweep. For the imaging, this effect is for example corrected in that the parallelepiped is cropped to form a cuboid.

There are various possibilities for taking into consideration the synchronicity of wavelength sweep and lateral displacement. If the detector lies close to an intermediate image plane, i.e. in a plane conjugate to the retina, the data of the three-dimensional parallelepiped are shifted with respect to each other. For each wave number $k_1$, an image of the sample can be added, wherein $I_i=I(k_i,x,y)$. These images $I_i$ are shifted somewhat with respect to each other. Since the assignment between lateral scan position and wave number is known, the entire wavelength adjustment can be assembled correspondingly for each location (x, y) in the sample. In this way, the three-dimensional data are assembled simply.

In example embodiments in which the detector is located in or near the conjugate pupil plane, it measures the Fourier transformation of the intensity distribution in the object plane (retina 2). A displacement in the object plane leads to a phase ramp in the detector plane. The correction of the simultaneous lateral adjustment by the scanner 13 and of the wavelength adjustment by the light source 4 is therefore a multiplication of the detector signal by a time-dependent phase ramp, which is proportional to the scan speed and the distance between pupil partial channel and optical axis in the pupil plane.

The optical set-up of FIGS. 1 to 3 de-couples the illumination and the capture of the measurement light from each other with respect to the optical properties and, in particular, the pupil size. In this way it is possible to optimize the illumination. For example, a Bessel-type illumination can be combined with a top hat cross-sectional profile for detection. In this way, in one embodiment achieves a high illumination depth, i.e. an illumination which is unchanged over a large z-range, and a high numerical aperture of the imaging at the same time. In the case of identical numerical aperture, an illumination focus of an extent of 1 mm would be achieved in z direction, for example with a Gaussian beam. In the case of a Bessel-type illumination, 2 to 3 mm extent is obtained in z direction. In this way, the optical resolution can be increased by 10 to 30% when the detection is done with a top hat-type profile.

A further example embodiment of the OCT uses a polarization splitting at the beam splitter 11. Such a thing is usually disadvantageous in the state of the art, and an intensity splitting is generally used. Polarization splitting is, surprisingly, advantageous for the described OCT, since polarized radiation entering the eye is changed with respect to its polarization state. Different structures of the eye have a different effect such that the polarization state of the backscattered signal is not unambiguously or clearly defined, but consists of components of different polarization state. This was also known in the state of the art and resulted in an intensity splitting being carried out, precisely because the backscattered radiation does not have a clearly defined polarization state. However, it was found that the measurement light is superimposed with the reference light and that only the components of the beams can interfere with each other, which have the same polarization state. Ultimately, the reference light therefore determines with its polarization state which portion of the measurement light can be utilized. Non-interfering portions fall on the detector and form an interfering background.

After the polarizing splitter 11, the illumination radiation B is linearly polarized. The lambda/4 plate 27, as is shown in FIG. 3, provides circularly polarized illumination radiation B at the eye 3. Backscattered measurement radiation M, which is likewise circularly polarized, is again linearly polarized by the lambda/4 plate, with the polarization direction being rotated by 90 degrees compared with the polarization direction of the illumination radiation B, which was emitted by the polarizing splitter 11. The measurement radiation M then passes through the polarizing splitter 11 without deflection and interferes with the reference radiation R, if this has the same polarization. This is the case when reference radiation R and illumination radiation B are identically linearly polarized after dividing from the source radiation. This is also the case when reference radiation R and illumination radiation B are circularly polarized after dividing from the source radiation and the reference radiation is linearly polarized identically to the measurement radiation M before superposition. Generally, it is of importance that the polarization splitting (e.g. by polarizing splitter 11 and plate 27) conditions the measurement radiation M and the reference beam path conditions the reference radiation R such that both radiations have the same polarization state at the detector.

This measure increases the signal-to-noise ratio, since only those parts of the measurement light are guided by the beam splitter 11 to the detector device 17 which are capable of interfering with the reference light. Thus, the polarization splitting which is actually disadvantageous and the discarding of a part of the measurement radiation M at the beam splitter 11 increases the quality of the signal.

In a further embodiment of the OCT, use is made of the fact that the illumination optical system 10 allows placement of the focus of the illumination radiation B at z position different from that of the focus which is predetermined by the detector optical system 14 for the collection of the measurement radiation M. Because of multiple scatterings in the retina, measurement radiation M from the retina can have the path length suitable for interference, but can propagate in another direction, which would limit the lateral resolution at depth. This effect can be compensated through different depth planes for illumination; and detection and the resolution at depth is optimized.

For image reconstruction from the detector signals according to the FD-OCT principle, it is necessary to know the current wavelength. This wavelength or the corresponding wave number k can be derived from controlling the light source 4. Alternatively, it is possible to couple out a beam portion and to record it in terms of the wavelength in order to know the current wavelength or the course of a wavelength sweep better.

Perpendicular to the scanning direction, detector channels can be binned in order to reduce speckle. This is particularly advantageous if only z sections through the retina are desired.

For a roughly resolved image, e.g. as preview, it is possible to add all or several detector channels. This is done after the corrections (e.g. aberration, z-position, total image generation) were made. The resolution of known OCT systems is obtained but with a higher signal-to-noise ratio and improved speckle behaviour, precisely because the combining is done after one or more of the corrections and goes beyond a normal pixel binning, thus.

If a detector is used which spatially resolves in only one direction, aberrations can also be corrected only in this direction. For particular applications this may be sufficient.

In one example embodiment a multilens array is arranged in front of the 2D detector 19 or in front of each of the 2D detectors 19a, 19b to improve a filling factor of an illumination of the pixels.

In one example embodiment, an iris camera is provided, which supports the user during the setting of the device to the eye position.

So far as method steps and/or signal corrections were described above, these are carried out in the OCT 1 by the control device C, which is connected to the detector/the detectors. The device reads the measurement signals of the detector/detectors and receives further data about the operation of the scanner 13 and the wavelength sweep and/or actuates such components correspondingly.

The invention claimed is:

1. An optical coherence tomograph for examining an eye, comprising:
   an illuminating device that provides source radiation that is sweepable in wavelength;
   an illumination and measurement beam path, which has a dividing element that divides the source radiation into illumination radiation and reference radiation, and the dividing element directs the illumination radiation to illuminate an illumination field in the eye with the illumination radiation and collects illumination radiation scattered back from the eye as measurement radiation, wherein the illumination and measurement beam path comprises a scanner that adjusts the lateral position of the illumination field in the eye and a front optical system;
   a reference beam path, which provides a first optical path length for the reference radiation which is the same as a second optical path length from the dividing element to the illumination field and back to a superimposition point;

a detection beam path, which receives the measurement radiation from the illumination and measurement beam path and the reference radiation from the reference beam path and superimposes the measurement radiation and the reference radiation at a superimposition point and guides the measurement radiation and the reference radiation onto at least one 2D detector;

wherein the illumination and measurement beam path further comprises a beam splitter that separates the measurement radiation collected from the eye from the illumination radiation guided to the eye, wherein the beam splitter guides separated measurement radiation to the detection beam path, and an optical element acting only on the illumination radiation, the optical element interacting with the front optical system and setting a numerical aperture of the illumination of the illumination field in the eye, wherein the detection beam path further comprises an optical element acting only on the measurement radiation, which optical element interacts with the front optical system and sets the numerical aperture with which measurement radiation is collected from the eye, and a diaphragm, which is arranged in front of the at least one 2D detector, and is arranged in or near to an intermediate image plane and defines the size of an object field from which the measurement radiation reaches the 2D detector, and wherein the at least one 2D detector comprises a spatial resolution having 4 to 100 pixels in a direction.

2. The optical coherence tomograph according to claim 1, wherein the at least one 2-D detector comprises a spatial resolution having 5 to 50 pixels in at least one direction.

3. The optical coherence tomograph according to claim 1, wherein the at least one 2-D detector comprises a spatial resolution having 5 to 40 pixels in at least one direction.

4. The optical coherence tomograph according to claim 1, wherein the at least one 2D detector lies in a plane which is conjugate to a plane in which the pupil of the eye lies.

5. The optical coherence tomograph according to claim 1, wherein the beam splitter is a polarizing beam splitter and a lambda/4 plate is arranged between the eye and the beam splitter, which plate filters the measurement radiation with respect to a polarization state which is matched to a polarization state of the reference radiation.

6. The optical coherence tomograph according to claim 1, wherein, the detection beam path comprises a beam splitter/combiner for balanced detection, which beam splitter/combiner conducts the reference radiation with the measurement radiation being superimposed in two different phase positions onto two 2D detectors.

7. The optical coherence tomograph according to claim 1, wherein the optical element acting only on the illumination radiation forms the illumination radiation into a Bessel beam.

8. The optical coherence tomograph according to claim 1, wherein the optical element acting only on the measurement radiation forms the measurement radiation into a bundle with a top hat cross-sectional profile.

9. The optical coherence tomograph according to claim 1, further comprising a control device, which controls the scanner for deflection during the wavelength tuning and generates or receives a scan signal which indicates a deflection state of the scanner, and is connected to the radiation source to read a wavelength signal which indicates a wavelength of the source radiation and thus of the illumination radiation and to the at least one 2D detector for reading measurement signals for each pixel, wherein the control device generates single images of the retina from the wavelength signal and the measurement signals and evaluates the scan signal to assemble the single images into a 3D total image.

10. The optical coherence tomograph according to claim 1, wherein the numerical aperture of the illumination and the numerical aperture with which measurement radiation is collected from the eye differ from each other.

11. The optical coherence tomograph according to claim 10, wherein the numerical aperture of the illumination is smaller than the numerical aperture with which measurement radiation is collected.

12. A method for optical coherence tomography for examining an eye, the method comprising:

providing source radiation, sweeping the wavelength thereof and dividing the source radiation into illumination radiation and reference radiation;

illuminating an illumination field of the eye with the illumination radiation and collecting illumination radiation scattered back from the eye as measurement radiation, using a scanner for adjusting the lateral position of the illumination field in the eye;

separating the measurement radiation collected at the eye from the illumination radiation guided to the eye;

defining a numerical aperture of the illumination of the illumination field of the eye by using an optical element acting only on the illumination radiation, and defining the numerical aperture with which measurement radiation is collected from the eye by using an optical element acting only on the measurement radiation;

superimposing the measurement radiation with the reference radiation and detecting an interference signal of the superimposed radiations with at least one 2D detector, which has a spatial resolution having 4 to 100 pixels in at least one direction; and using a diaphragm, which is arranged in front of the at least one 2D detector and is arranged in or near to an intermediate image plane in order to define the size of an object field from which the measurement radiation reaches the 2D detector.

13. The method according to claim 12, wherein the at least one 2-D detector comprises 5 to 50 pixels in the at least one direction.

14. The method according to claim 12, wherein the at least one 2-D detector comprises 5 to 40 pixels in the at least one direction.

15. The method according to claim 12, further comprising arranging the at least one 2D detector in a plane which is conjugate to a plane in which the pupil of the eye lies.

16. The method according to claim 12, further comprising:

separating the measurement radiation collected from the eye from the illumination radiation guided to the eye by a polarization splitting;

filtering the measurement radiation with respect to a polarization state which is matched to a polarization state the reference radiation has during the superimposition; and discarding wherein portions of the measurement radiation not corresponding to this polarization state.

17. The method according to claim 12, further comprising utilizing balanced detection for the detection of the interference signal.

18. Based The method according to claim 12, further comprising forming the illumination radiation to a Bessel beam.

19. The method according to claim 12, further comprising forming the measurement radiation into a bundle with a top hat cross-sectional profile.

20. The method according to claim 12, further comprising controlling the scanner for the deflection during the wavelength sweep and generating single images of the retina from measurement signals of the 2D detector and a wavelength signal and assembling the single images into a 3D total image taking into consideration the deflection state of the scanner.

21. The method according to claim 12, wherein the numerical aperture of the illumination and the numerical aperture with which measurement radiation is collected from the eye differ from each other.

22. The method according to claim 21, wherein the numerical aperture of the illumination is smaller than the numerical aperture with which measurement radiation is collected.

\* \* \* \* \*

UNITED STATES PATENT AND TRADEMARK OFFICE
CERTIFICATE OF CORRECTION

PATENT NO. : 10,568,503 B2
APPLICATION NO. : 15/519378
DATED : February 25, 2020
INVENTOR(S) : Daniel Bublitz et al.

Page 1 of 1

It is certified that error appears in the above-identified patent and that said Letters Patent is hereby corrected as shown below:

In the Claims

Column 19, Line 1, delete "Based"

Signed and Sealed this
Fifth Day of May, 2020

Andrei Iancu
*Director of the United States Patent and Trademark Office*